United States Patent [19]

Kobayashi

[11] Patent Number: 4,563,674

[45] Date of Patent: Jan. 7, 1986

[54] OIL LEAK DETECTOR

[75] Inventor: Satoru Kobayashi, Hitaka, Japan

[73] Assignee: Junkosha Company Ltd., Tokyo, Japan

[21] Appl. No.: 531,749

[22] Filed: Sep. 13, 1983

[30] Foreign Application Priority Data

Sep. 16, 1982 [JP] Japan .............................. 57-140132

[51] Int. Cl.[4] .............................................. G08B 21/00
[52] U.S. Cl. .................................... 340/620; 210/315; 210/924; 324/65 P; 340/605
[58] Field of Search ............... 340/602, 604, 620, 605; 324/65 P; 210/85 R, 96.1, 924, 315; 73/304 R

[56] References Cited

U.S. PATENT DOCUMENTS

| 4,111,813 | 9/1978 | Preus ................... | 210/924 X |
| 4,366,067 | 12/1982 | Golding et al. ........ | 210/924 X |
| 4,395,336 | 7/1983 | Eng .................... | 210/924 X |
| 4,439,324 | 3/1984 | Crotti .................. | 210/924 X |

Primary Examiner—James L. Rowland
Assistant Examiner—Daniel Myer
Attorney, Agent, or Firm—Mortenson & Uebler

[57] ABSTRACT

An improved floating sensor for the detection of oil leaks at a water surface is provided wherein a cloth layer is affixed to the outside of a leak detector which, by capillary action, results in a threshold level of oil film thickness below which no alarm sounds and above which an alarm will sound. The invention provides means for the pre-selection of the thickness of oil film which will be detected and eliminates the detection of very thin, inconsequential oil leaks.

4 Claims, 5 Drawing Figures

OIL LEAK DETECTOR

BACKGROUND OF THE INVENTION

The present invention relates to floating apparatus for detecting oil floating on the surface of water and, more particularly, to such an apparatus which has a detecting device comprising electrically conductive, expanded, porous polytetrafluoroethylene (PTFE), or similar material, which absorbs oil thereby causing a change in the electrical conductivity of the material and is detected, and which has a layer of cloth attached to the outer surface of the detecting device resulting in the water level around the detector device being higher than the general surface of the water, whereby the thickness of oil film to which the apparatus responds can be pre-selected.

SUMMARY OF THE INVENTION

Apparatus for detecting oil floating on the surface of water is provided, comprising a detecting device floating on the surface of said water capable of absorbing oil floating on the surface of the water, the detecting device having warning means which is operated according to a change in the electrical conductivity of the detecting device that is caused by absorption of oil, and a layer of cloth affixed outside the detecting device such that it forms a boundary of water at a height above the general surface of the water and on the outer periphery of the detecting device. The layer of cloth may be disposed on the outer periphery of the detecting device or on the outer periphery of a housing containing the detecting device. The detecting device may include an oil absorbing material on the outer periphery thereof.

DETAILED DESCRIPTION OF THE INVENTION AND PREFERRED EMBODIMENTS WITH REFERENCE TO THE DRAWINGS

An improved floating sensor for the detection of oil leaks at a water surface is provided wherein a cloth layer is affixed to the outside of a leak detector which, by capillary action, results in a threshold level of oil film thickness below which no alarm sounds and above which an alarm will sound. The invention provides means for the pre-selection of the thickness of oil film which will be detected and eliminates the detection of very thin, inconsequential oil leaks.

Figure 1:
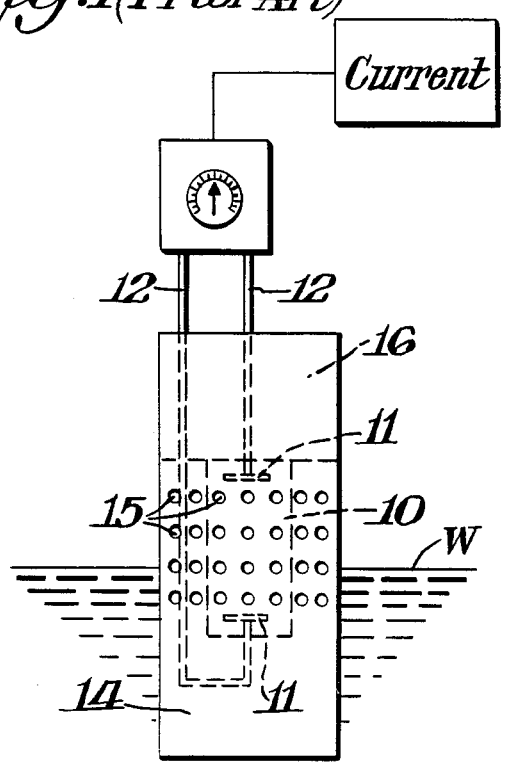
FIG. 1 is a front elevation of a conventional oil leak detecting device.

The detecting section of a conventional apparatus for detecting oil on the surface of water which has leaked from a tank in an oil storage base, or the like is shown in FIG. 1, in which a detecting device 10 is formed from an electrically conductive material, for example, expanded, porous polytetrafluoroethylene to which a filler, e.g., carbon black, has been added. The conductive material is formed into a thin sheet. Electrodes 11 are attached to the upper and lower ends of the detecting device 10, and lead wires 12 are connected to the electrodes 11 so that the device can be energized. A housing 14, preferably made of polyvinyl chloride is provided, with the periphery of its central portion provided with a plurality of small holes 15. The detecting device 10 is housed in housing 14, and the lead wires 12 extend outside of the housing.

When the apparatus is immersed in water, the detecting section assumes an upright posture, and the apparatus floats on the water in such a manner that the portion of the housing 14 above the portion provided with the small holes 15 is held above the water. If necessary, a float (not shown) may be used.

When oil floating on the water is to be detected by the above-mentioned detecting section, the device is placed in water. Then, the lead wires 12 of the detecting device 10 are connected to warning means so that the power supply incorporated in the warning means supplies electric power to the detecting device 10. Because PTFE is impervious to water, no water flows into device 10. When oil flows over the water, forms a film, and spreads over the water, the oil flows through the small holes 15 formed around the periphery of the housing 14 of the detecting section floating on the water. Then, because PTFE can absorb oil, the device 10 absorbs the oil causing a change in the electrical resistance of the device 10. This, in turn, produces a change in the current flowing into the detecting device 10, and this change is detected by the detecting circuit incorporated in the warning means to issue a warning.

The principle on which the detecting apparatus described above operates is as follows. The expanded, porous polytetrafluoroethylene constituting the detecting device has a microstructure composed of nodes connected together by a number of minute fibrils. Since the fibrils are separated from one another leaving openings among them, the microstructure has a high porosity and allows oil, whose surface tension is smaller than that of water, to penetrate and to be absorbed, but the PTFE is impervious to water. The absorption causes a change in the electrical resistance which results in a corresponding change in current. This variation in current is detected by energizing the expanded, porous polytetrafluoroethylene, to which conductivity has been imparted by the addition of, say, carbon black, by the use of the aforementioned characteristics of this material.

When the above-mentioned detecting section is afloat, the water line around the detecting device 10 is substantially at the same level as the general surface of the water.

Accordingly, even when an oil film which has flowed over the water is very thin, the detecting apparatus is operated. Thus, it is impossible to operate the apparatus only when the thickness of an oil film exceeds a predetermined value, or to change the thickness of oil membranes to which the apparatus responds.

It is an object of the present invention to provide a detecting apparatus equipped with a detecting section which is capable of pre-selection of the thickness of oil membrane to which it responds, thus solving the foregoing difficulties.

As can be seen from the embodiments described herein in connection with the accompanying drawings, the apparatus for detecting oil floating on the surface of water in accordance with the present invention comprises a detecting device 10 and an over-layer of cloth 20. The device 10 comprises electrically conductive, expanded polytetrafluoroethylene, or similar material, containing an electrically conductive filler, and having electrodes 11 installed in its upper and lower ends, for example, so as to be energized. The device 10 is housed in a container consisting of a housing 14, the periphery of which is provided with a plurality of small holes 15. The space inside of the container above the conductive PTFE can be filled with electrically insulating material 16. The device 10 is comprised of a detecting section constructed so as to be capable of floating upright on the surface of water, and warning means connected to the detecting section. When the detecting section of the detecting device 10 absorbs oil, a change in electrical resistance takes place. This utilized in detecting oil floating on the surface of the water. According to the present invention, the outer periphery of either the detecting device 10 or the housing 20 is covered with a cloth 20 extending from a height below the water line of the device or housing to a height above the water line to make the water absorbing level Y for the device 10 higher than the water W by a value equivalent to a given thickness of oil film, so that a boundary of water is formed on the outer periphery of the detecting device above the general surface of the water. Embodiments of the present invention are hereinafter described with reference to the drawings.

Figure 2A:
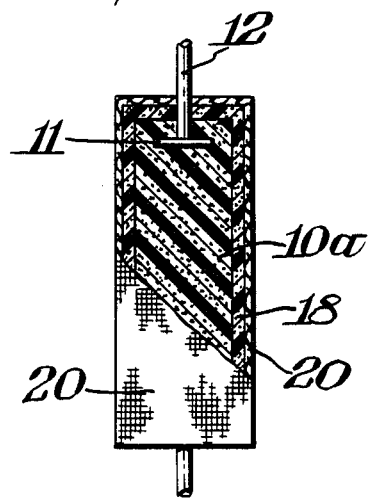
FIG. 2(a) is a front elevation of a detecting device according to this invention, partially in cross-section.
Figure 2B:
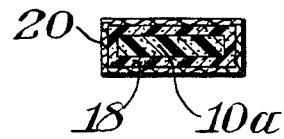
FIG. 2(b) is a cross-sectional view of the detecting device shown in FIG. 2(a).

FIGS. 2(a) and 2(b) illustrate embodiments of detecting device 10 according to the invention. The body of the detecting device is indicated by reference to numeral 10a and has the same construction as that of the detecting device previously described in connection with FIG. 1. Hence, like components are denoted by like reference numerals and will not be described below.

A layer 18 consisting of a material which absorbs oil well can be deposited on the surface of the body 10a of the detecting device. Formed on the oil absorbing layer 18 is a layer of cloth 20, which is made of a sheet of woven or nonwoven fabric made from threads having a large or small water absorption, or absorbing no water, as desired.

By constructing the detecting section using the detecting device 10a such that the oil absorbing layer 18 and the cloth layer 20 are formed on the surface of the body 10a as described thus far, when the detecting section is placed in water and made to float, the water level around the detecting device 10a is higher than the general surface of the water, because water is drawn into the mesh in the structure of the cloth layer 20 by virtue of capillary action in the layer 20 attached to the outer surface of the device 10a.

Figure 3:
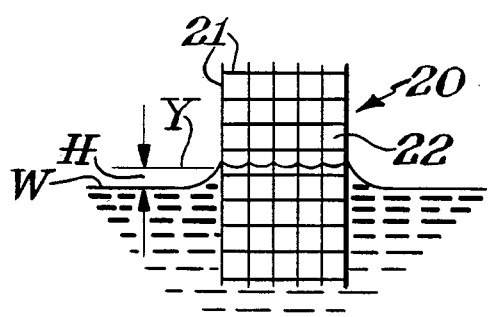
FIGS. 3 and 4 show the effect of the water levels around two embodiments of the leak detecting device of this invention.

FIG. 3 shows the water absorbing level for the detecting device of this invention when the layer of cloth 20 consists of fabric made of threads having high water absorption. Water is sucked into the mesh 22 of the warp 21 of the cloth layer, 20, during which the water surface takes a wavy form. Elevation of water in the layer 20 by capillary action renders the water absorbing level Y for the detecting device higher than the surface of the water W by the value H.

Figure 4:
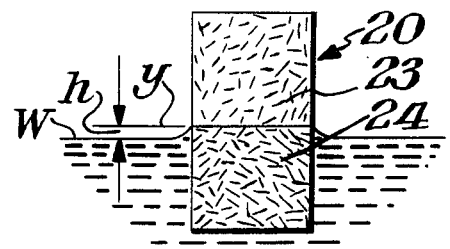

FIG. 4 shows the water level in the detecting device when the cloth layer consists of a sheet of nonwoven cloth made of threads having relatively low water absorption. Water is sucked into the mesh 24 of the threads 23 of the cloth layer 20 and it forms a relatively flat level. Again, the water absorbing level y of the detecting device is higher than the surface of the water W by the value of h because of the elevation of water in the layer 20 by capillary action.

When the water absorbing level Y for the detecting device 10a is higher than the surface of the water W as stated above, if the thickness of oil film on the water is smaller than the height H of water around the device 10a above the general surface of the water, then the oil is unable to make contact with the surface of the device 10a. But if an oil film whose thickness is greater than the water height H around the device 10 above the surface of the water is encountered, then the oil can rise above the water absorbing level Y and contact the device.

The water height H in the detecting device 10a can be pre-set to a desired value by appropriately selecting the kind of cloth used in layer 20 formed on the device 10a by virtue of the thread structure of the woven or nonwoven fabric, the thickness of the fabric, the dimensions of the mesh, etc. In a case where a layer of cloth having a high water absorption is used, the water height H required for the detecting device 10a can be determined by setting the upper end of the cloth layer to a given position above the water line of the device 10a. In a case where a layer of cloth having a low water absorption is used, the upper end of the cloth layer may be set either to the upper end of the detecting device or to a position higher than the water line of the detecting device by an appropriate value. In either case, the lower end of the cloth layer may be set either to the lower end of the detecting device or to a position somewhat lower than the water line of the detecting device.

When an oil film having a thickness exceeding the water height H around the detecting device 10a contacts the device 10a, the oil passes the upper fringe of the cloth layer 20, or enters the mesh of the layer 20, and permeates the layer 18 of the oil absorbing material. Then, the permeated oil is absorbed by the body 10a of the detecting device.

Although the cloth layer 20 is attached to the body of the detecting device via the layer of the oil absorbing material 18 in the aforementioned embodiments, the oil absorbing layer 18 can be omitted as needed.

Also, in the embodiments described above, the cloth layer 20 is arranged on the outer periphery of the detecting device. Alternatively, the cloth layer may be disposed on the outer periphery of a housing rather than directly disposed on the periphery of the detecting device. In this alternative construction, the body of the detecting device and the inner surface of the container are similarly shaped to bring the body of the detecting device into contact with the inner surface of the container, or otherwise the layer of the oil absorbing material can be interposed between the body of the detecting device and the inner surface of the container for insulation.

As described hereinabove, the present invention provides a layer of cloth attached to the outer periphery of either a detecting device comprising electrically conductive, expanded, porous polytetrafluoroethylene, or the like, or to the outside of a container housing the detecting device, to form a boundary of water which makes the water absorbing level on the outer periphery of the detecting device higher than the general surface of water. Accordingly, the water height around the detecting device above the surface of the water can be altered by changing the kind, position, or other parameters of the cloth layer, in accordance with the invention. Consequently, the thickness of an oil film to which the detecting device responds can be varied and pre-selected, whereby the detecting apparatus can enjoy wide application.

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

What is claimed is:

1. Apparatus for detecting oil floating on the surface of water, the apparatus comprising:
    a detecting device floating on the surface of said water and capable of absorbing oil floating on the surface of said water, the detecting device having warning means which is operated according to a change in the electrical conductivity of the detecting device that is caused by absorption of oil, and
    a layer of cloth affixed outside said detecting device such that it forms a boundary of water at a height above the general surface of the water adjacent the outer periphery of said apparatus.

2. Apparatus for detecting oil floating on the surface of water as set forth in claim 1, wherein the layer of cloth is disposed on the outer periphery of said detecting device.

3. Apparatus for detecting oil floating on the surface of water as set forth in claim 1, wherein the layer of cloth is disposed on the outer periphery of a housing containing said detecting device.

4. Apparatus for detecting oil floating on the surface of water as set forth in any of claims 1-3, wherein said detecting device has a layer of an oil absorbing material on the outer periphery thereof and said cloth layer is disposed on the outer periphery of said oil absorbing material.

* * * * *